United States Patent [19]
Gilmore et al.

[11] Patent Number: 4,924,477
[45] Date of Patent: May 8, 1990

[54] ASSEMBLY AND METHOD FOR DETERMINING THE COEFFICIENT OF THERMAL EXPANSION OF A WORKPIECE

[75] Inventors: James F. Gilmore, Rochester; Carl A. Lloyd, East Bloomfield; Charles S. Kirk, Rochester, all of N.Y.

[73] Assignee: Eastman Kodak Company, Rochester, N.Y.

[21] Appl. No.: 301,211

[22] Filed: Jan. 24, 1989

[51] Int. Cl.$^5$ .................. G01N 25/16; G01B 11/02
[52] U.S. Cl. ....................... 374/55; 356/358; 269/55; 364/562
[58] Field of Search ............. 374/55, 56, 45; 356/357, 358; 364/562; 269/55

[56] References Cited

U.S. PATENT DOCUMENTS

| | | | |
|---|---|---|---|
| 2,689,474 | 9/1954 | Wachtel | 374/50 |
| 3,176,499 | 4/1965 | Sikora | 374/50 |
| 3,898,836 | 8/1975 | Clusener | 73/16 |
| 4,282,688 | 8/1981 | Krim | 350/253 |
| 4,643,577 | 2/1987 | Roth et al. | 356/358 |

FOREIGN PATENT DOCUMENTS

| | | | |
|---|---|---|---|
| 3514000 | 10/1986 | Fed. Rep. of Germany | 374/55 |
| 63-148154 | 6/1988 | Japan | 374/55 |

OTHER PUBLICATIONS

Ruffino, et al., "Fast Interferometric Dilatometer", AIP Conf. Proc. (U.S.A.), no. 17 (1973), pp. 159–166.
Wielke, B., "A Variable Temperature, Tensile Testing Cryostat", Cryogenics, vol. 16, No. 2, pp. 110–112, (Feb. 1976).
Kirchner, T. L., "Laser Interferometer System for the Measurement of Creep in Pressurized Tubes", Laser & Electro-Optic (Germany), vol. 9, pp. 30–31, 34–36 (1977).
Blankinship, E. A., "An Automated Optical Dilatometer for Inhomogeneously Expanding Material", AIP Conf. Proc. (U.S.A.), no. 17 (1973).
Okaji, M. et al., "An Interferometric Dilatometer and Supporting Systems of the Specimen", Oyo Bukuri (Japan), vol. 50, No. 7 (Jul. 1981).

*Primary Examiner*—William A. Cuchlinski, Jr.
*Assistant Examiner*—Diego F. F. Gutierrez
*Attorney, Agent, or Firm*—Stephen C. Kaufman

[57] ABSTRACT

An assembly and method suitable for determining the coefficient of thermal expansion (CTE) of a workpiece. The assembly includes a dual channel laser interferometer system placed in operative association with the workpiece, and a vacuum, heating and cooling chamber surrounding the workpiece. The assembly is particularly useful for determining the CTE of a workpiece having a relatively low value, e.g., a CTE less than $0.1 \times 10^{-6}$ inch/inch °F. It is therefore advantageously employed for determining the CTE of a workpiece comprising a composite, like a graphite/epoxy composite, that may have a CTE in the range of $\pm 0.2 \times 10^{-6}$ inch/inch °F.

20 Claims, 3 Drawing Sheets

ASSEMBLY AND METHOD FOR DETERMINING THE COEFFICIENT OF THERMAL EXPANSION OF A WORKPIECE

BACKGROUND OF THE INVENTION

Cross-Reference To A Related Application

This application is related to a copending and commonly assigned patent application Ser. No. 301,210 filed January 24, 1989 to Gilmore et al, which is being filed contemporaneously with this application. The entire disclosure of this copending application is incorporated by reference herein.

Field of the Invention

This invention relates to an assembly and method suitable for determining the coefficient of thermal expansion of a workpiece.

Introduction to the Invention

The coefficient of thermal expansion (CTE) of a workpiece provides a measure of the deformations induced in the workpiece by a change in temperature. The CTE may be expressed by a well-known equation (1):

$$CTE = \frac{\Delta L}{L \Delta T°} \quad (1)$$

where
L = length of a workpiece having a uniform thermal strain; and
ΔL = a linear deformation due to a change in temperature of ΔT°.

It is important to know the coefficient of thermal expansion, for example, when the workpiece is part of a statically indeterminate system. Here, expansions or contractions of the workpiece, induced by a change of temperature, may be inhibited or entirely prevented in certain directions. This, in turn, may cause significant stresses in the system, which stresses may have to be investigated by way of the coefficient of thermal expansion, and subsequently accommodated by the system.

SUMMARY OF THE INVENTION

Our motivation for providing a novel assembly and method, suitable for determining the CTE of a workpiece, comes about in the following way. We are working with workpieces that comprise novel compositions; that may be utilized in systems of exceptional sensitivity and high performance; and which may be subjected to unusual thermal stresses. For example, the workpiece may comprise a critical component of an optics device that is mounted in a spacecraft. To the end of designing a workpiece to ensure a desired system performance, we determine its coefficient of thermal expansion. The CTE'S of our workpieces comprise an unusually wide range of values, e.g., from $0.2 \times 10^{-6}$ inch/inch °F. to $-0.2 \times 10^{-6}$ inch/inch °F.

In general, techniques for determining the CTE of a workpiece follow equation (1) above, which instructs one to determine ΔT and ΔL. Conventional techniques for determining the CTE of a workpiece are set forth in the ASTM Standards. We have found that these conventional techniques may be adequate when the required CTE is approximately $12 \times 10^{-6}$ inch/inch °F., or greater. Conventional techniques may be acceptable, therefore, for determining the CTE of a "pure" workpiece, such as aluminum, which has a CTE of 12.9 inch-h/inch °F. On the other hand, we have found that conventional techniques may not be suitable for the case where:

(1) the workpiece has a relatively much lower CTE than the last cited figure, say a CTE of less than $0.1 \times 10^{-6}$ inch/inch °F.; and/or (2) the workpiece comprises a composition that is not explicitly recited by the ASTM in its catalogue of CTE testing procedures. An example here is a workpiece comprising a composite e.g., a graphite/epoxy composite, or graphite/glass composite. It is noted that the CTE of the first composite may be as low as $0.03 \times 10^{-6}$ inch/inch °F., which is less than that of pure aluminum, and by approximately three orders of magnitude.

The deficiencies of the conventional techniques for determining the CTE of materials having a relatively low CTE value, and/or a novel composition, may include the introduction of systematic and random errors. Systematic errors result from the use of imperfect measuring instruments or methods of measurement not justified under the existing conditions. Random errors, on the other hand, result from limitations in the observer's skill or judgment and from influences, such as minute fluctuations in physical conditions, beyond the control of the observer.

As noted, since we are making increasing use of workpieces which comprise a wide range of coefficients of thermal expansion and are of novel composition, we have turned our attention from conventional ASTM CTE measuring techniques, to other techniques.

One non-ASTM technique is disclosed in the article by E.G. Wolff and S.A. Eselun, "Double Michelson Interferometer For Contactless Thermal Expansion Measurements", Proceedings of the Society of Photo-Optical Instrumentation Engineers, Vol. 192, pp. 204–208, August, 1979. Wolff et al. disclose a single laser interferometer system (see Wolff et al. FIG. 1). In one embodiment, they split a single laser beam, by way of beamsplitters, into a reference standard beam, and a sample (or workpiece) beam, and determine the length ΔL of the sample by way of the reference standard beam. The temperature ΔT of the sample is determined by way of thermocouples. Wolff et al. determine the CTE of a fused silica standard, and they are silent on the use of their single laser interferometer system to determine the CTE of a composite. It is unclear that Wolff et al. avoid the noted problem of systematic and random errors that may render nugatory nominal testing results, especially when a CTE is in the range of less than $0.1 \times 10^{-6}$ inch/inch °F.

Other non-ASTM techniques and/or materials relating to the coefficient of thermal expansion are referenced, for example, in S. F. Jacobs, "Dimensional Stability Of Materials Useful In Optical Engineering"; and S. F. Jacobs, J. N. Bradford and J. W. Ill, "Ultraprecise Measurement Of Thermal Coefficients Of Expansion", Opt. 9, 2477 (1970).

We have now discovered a novel assembly and method suitable for determining a coefficient of thermal expansion of a workpiece. In a first aspect, the present invention comprises an assembly comprising:

(a) a chamber which surrounds and is spaced apart from the workpiece;

(b) means for locating the workpiece in the chamber;

(c) means for selectively changing and monitoring the temperature of the workpiece;
(d) a dual channel laser interferometer system placed in operative association with the workpiece so that, under testing conditions, information concerning the length of the workpiece is obtained; and
(e) a data acquisition system for computing the coefficient of thermal expansion of the workpiece based on the temperature and lenght of the workpiece under test.

The assembly of the present invention includes a dual channel laser interferometer system. We have recognized that this system, in combination with the other elements as defined, has the advantage of appreciably increasing a signal (i.e., a desired CTE measurement) to noise ratio, compared to say, the previously discussed Wolf et al. technique. This advantage is obtained in the following way. Our use of the dual channel laser eliminates a dependency on a reference standard beam (cf., Wolfe et al., above), which reference beam itself can be the carrier of systematic and/or random errors that may swamp out the signal.

Complementary to this advantage is the fact that the accuracy of the present invention, which is the degree of conformity of a measured or calculated value to some recognized standard or specified value, is such that any systematic errors cannot vitiate the accuracy of our determined CTE. In particular, the novel assembly can determine a CTE within $\pm 1.7 \times 10^{-8}$ inch/inch °F. of a specified CTE.

The assembly of the present invention is particularly useful for determining the coefficient of thermal expansion of a workpiece having a relatively low value, for example, less than $0.1 \times 10^{-6}$ inch/inch °F., especially less than $0.03 \times 10^{-6}$ inch/inch °F. It is therefore advantageously employed for determining the CTE of composites like graphite/epoxy composites that can have a CTE in the range from $0.2 \times 10^{-6}$ inch/inch °F. to $-0.2 \times 10^{-6}$ inch/inch °F.

In another aspect, the present invention provides a method for determining the coefficient of thermal expansion of a workpiece, which method comprises:
(a) locating the workpiece in a chamber which surrounds and is spaced apart from the workpiece;
(b) changing the temperature of the chamber, which in turn, causes the temperature of the workpiece to change from an arbitrary and known state to a measurable isothermal state; and
(c) placing in operative association with the workpiece a dual channel laser beam for obtaining information concerning the change in length of the workpiece, as the chamber temperature changes from the arbitrary and known state to the isothermal state.

BRIEF DESCRIPTION OF THE DRAWINGS

The invention is illustrated in the accompanying drawing, in which.

DETAILED DESCRIPTION OF THE INVENTION

Figure 1:
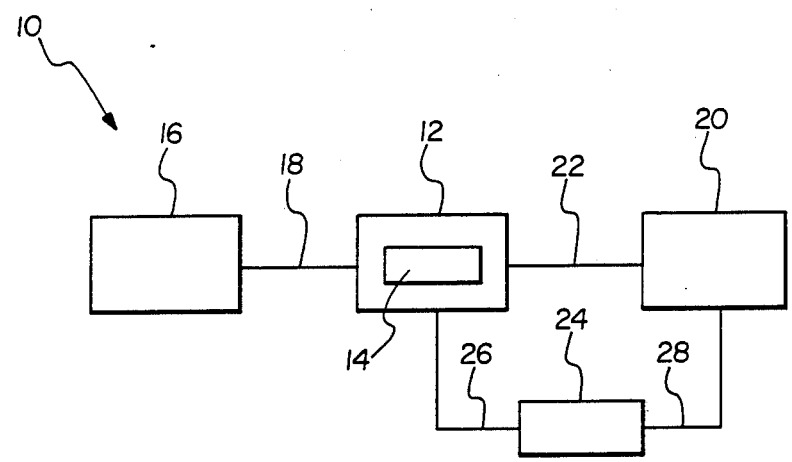
FIG. 1 is a generalized diagram of the assembly of the present invention.

Attention is now directed to the drawings. FIG. 1 provides a generalized diagram of an assembly 10 of the present invention. The assembly 10 comprises a chamber 12 which surrounds and is spaced apart from a workpiece 14; a vacuum, heating and cooling system 16 which is connected along a line 18 to the chamber 12; a dual channel laser interferometer system 20 placed in operative association with the workpiece 14, as shown by a line 22; and a data acquisition system 24, which receives workpiece 14 temperature information along a line 26 from the chamber 12, and workpiece 14 length information along a line 28 from the laser interferometer system 20.

Figure 2:
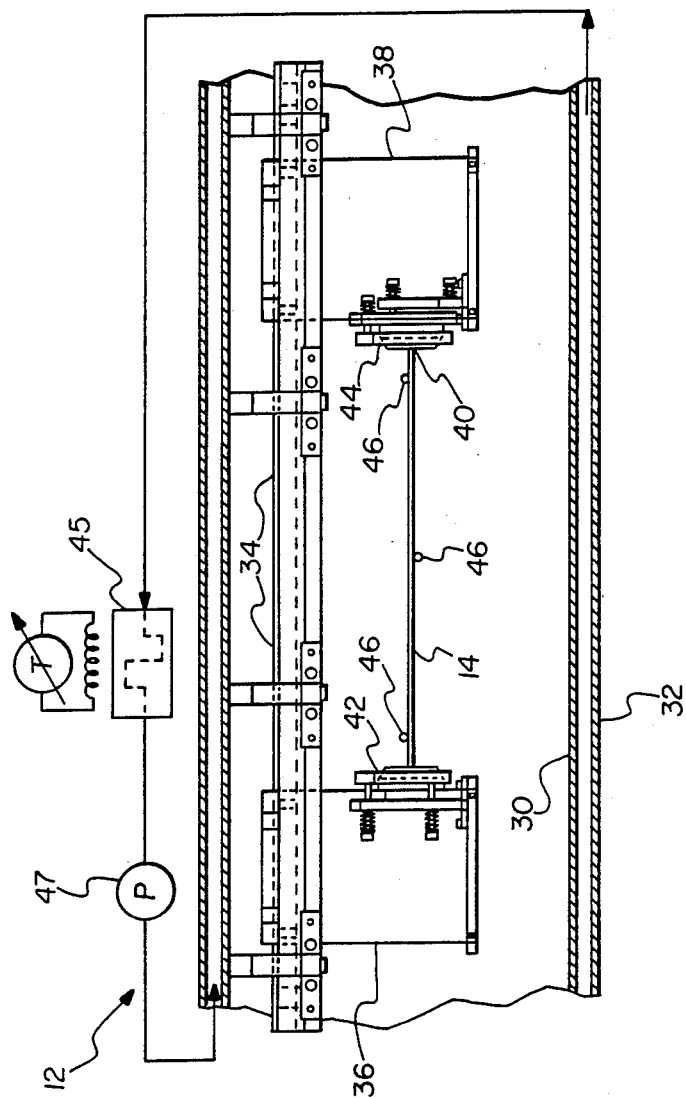
FIG. 2 is a diagram of a chamber and support apparatus of the present invention.

FIG. 2 shows details of the FIG. 1 chamber 12. Preferably, the chamber 12 comprises inner and outer walls 30, 32 which form a water jacket to heat and cool the workpiece 14. The chamber 12 preferably comprises aluminum, in order to readily conduct heat and to provide a uniform temperature gradient, and is preferably insulated to help stabilize the chamber 12 temperature. The chamber 12 may alternatively comprise copper, invar, or steel. The chamber 12 preferably is positioned on an isolation table, not shown, in order to provide a stable surface for the chamber 12 and the laser interferometer system 20. An optically transparent window or similar known means is provided for introducing the laser beam into the chamber.

The chamber 12 includes a means for locating the workpiece 14 in the chamber 12. The means preferably comprises a rail assembly 34; a first and second flexure system 36, 38 connected to the rail assembly 34; and a means 40 for engaging the workpiece 14 to the first and second flexure systems, respectively. We now discuss these elements, one at a time. The rail assembly 34 facilitates loading and unloading sundry workpieces. The rail assembly is preferably epoxied to the chamber 12 inner walls. The first and second flexure systems 36, 38 preferably comprise an invar composition to minimize distortion and associated errors. The means 40 for engaging the workpiece 14 to the first and second flexure systems 36, 38, preferably comprises a ball and socket arrangement which engage the workpiece 14 by way of first and second imaging devices 42, 44, attachable to either ends of the workpiece at first and second locations, as discussed in more detail below.

The flexure system 36, 38 just disclosed provides a solution to a problem we have identified, namely, that a workpiece undergoing expansions or contractions during testing, may shift or tilt the imaging devices 42, 44 out of alignment with the laser interferometer system 20. The flexure system 36, 38, however, accommodates such expansions or contractions so that, for example, a desired parallelism between the laser interferimeter system 20 and the imaging devices is always maintained.

The chamber 12, as shown in FIG. 1, receives along the line 18 various inputs from the vacuum, heating and cooling system 16. In particular, the system 16 preferably evacuates the chamber 12 down to approximately $1 \times 10^{-3}$ Torr, thus reducing measurement errors due to air currents, and controls a bath temperature in accordance with known techniques to within $\pm 0.5°$ F., and preferably to within $\pm 0.041°$ F. The temperature of the workpiece 14 is preferably monitored by way of a plurality of thermistors 46 directly attached to different portions of the workpiece 14, and providing an output to the data acquisition system 24. Alternatively, thermocouples may be used. Conventional equipment can be used for these purposes, including, for example, a Neslab Model No. RTE-110 constant temperature bath and circulator 45, and a Trivac Model No. D4A rotary vane pump 47.

Figure 3:
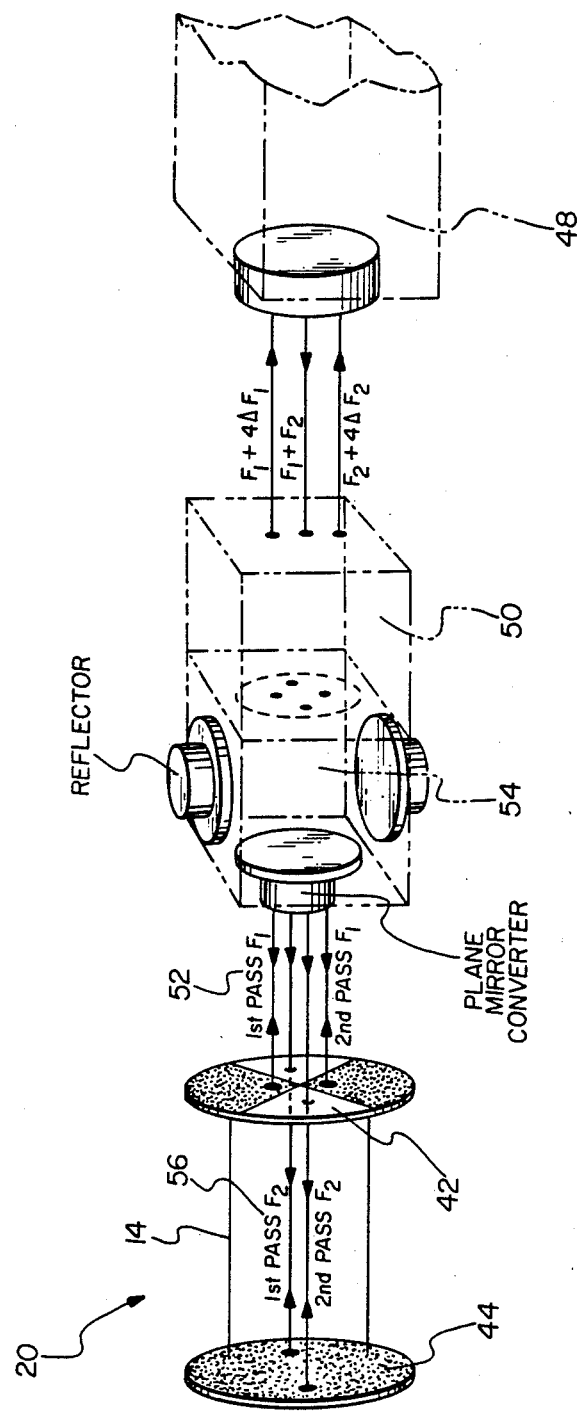
FIG. 3 is a diagram of a dual channel laser interferometer system used in the assembly and method of the present invention.

Attention is now directed to FIG. 3, which shows details of the dual channel laser interferometer system 20, which inputs to the data acquisition system 24. A preferred system 20 is available as Hewlett Packard Model 5526A, and a preferred system 24 is available as Hewlett Packard Model 86B personal computer with custom designed electronic boxes. The system 20 includes a laser head 48 that emits a two frequency laser beam, and preferably comprises a helium-neon laser having a main spectral line of 6328 Å. The two frequencies may be separated from each other in a dilatometer converter 50, by way of filters. The two frequencies are preferably separated by approximately 2 Mhz. One frequency, called a first frequency ($F_1$) measurement beam 52, is directed to a remote interferometer 54, the remote interferometer 54 comprising appropriate reflectors and a plane mirror converter. The first frequency ($F_1$) measurement beam 52 is optically processed so that it can travel four times between the aforementioned first imaging device 42 and the remote interferometer 54, being reflected two times off the device 42. In particular, the first imaging device 42 preferably comprises first and second specular reflector portions, located in diagonally opposite first and third quadrants with corresponding parts separated by a 180° angle (for example, the leading edges of the I and III quadrants will be separated by a 180° angle), for serially reflecting the first frequency ($F_1$) measurement beam 52 first from the first portion, then from the second portion, back and forth to the remote interferometer 54 reflectors. Continuing, the second separated frequency, called a second frequency ($F_2$) measurement beam 56, is optically processed so that it can (1) pass first through one and then the other of first and second non-reflective portions, located in diagonally opposite second and fourth quadrants with corresponding parts separated by a 180° angle, of the first imaging device 42; (2) reflect serially two times off the aforementioned second imaging device 44; and (3) return to the remote interferometer 54 thus traveling four times between the second imaging device and the interferometer 54. The second imaging device 44 preferably comprises a flat mirror.

The method/operation of the assembly 10 of FIGS. 1, 2, 3 is as follows. A workpiece 14 of known length L, for example, one comprising a graphite/epoxy composite, is located in the chamber 12 by way of the rail assembly 34. The first and second flexure systems 36, 38 engage opposite ends of the workpiece 14, as well as the first and second imaging devices 42, 44 located on either end of the workpiece 14. The imaging devices 42, 44 are located substantially on the normal to the dual frequency laser beam, as indicated by the FIG. 1 line 22. The workpiece 14 is allowed to reach a steady-state temperature, at an arbitrary but known temperature $t_1$. This step is effected by way of the system 16, and the temperature $t_1$, monitored by the thermistors 46, is recorded by the data acquisition system 24. Next, the temperature of the chamber 12 is changed again by way of the system 16, and the workpiece 14 begins to expand or contract, as it starts to equilibrate to an isothermal state, $t_2$, as measured by the thermistors 46.

As the workpiece 14 expands or contracts in response to the change in temperature $\Delta t = t_2 - t_1$, the first and second imaging devices 42, 44, attached to the workpiece 14, also move in correspondence. At the same time, the first frequency ($F_1$) reference beam 52, and the second frequency ($F_2$) measurement beam 56 traverse the two-fold optical paths described above. Since, in fact, the imaging devices 42, 44 are now moving with the workpiece 14, frequency shifts are induced in the beams 52, 56. In particular, the first frequency ($F_1$) measurement beam 52 traverses a variable optical path given by the expression $F_1 + 4\Delta F_1$; the second frequency ($F_2$) measurement beam 56 traverses a variable optical path given by the expression $F_2 + 4\Delta F_2$. The ratio $$\frac{F_1 + 4\Delta F_1}{F_2 + 4\Delta F_2},$$

in turn, expresses the relative (Doppler) frequency shifts of the two beams 52, 56, and corresponds to the desired expansion/contraction parameter $\Delta L$ of the workpiece 14. That is, the laser interferometer system 20 converts the frequency shift ratio $$\frac{F_1 + 4\Delta F_1}{F_2 + 4\Delta F_2}$$

into displacements, and subtracts the one imaging device 42 displacement from the second imaging device 44 displacement, to calculate the relative displacement $\Delta L$ between the two imaging devices. Finally, the data acquisition system 24 uses this information to determine the CTE of the workpiece 14, in accordance with equation (1) supra.

What is claimed:

1. An assembly suitable for determining a coefficient of thermal expansion of a workpiece having opposite ends, the assembly comprising:
   (a) a chamber which surrounds and is spaced apart from the workpiece;
   (b) means for locating the workpiece in the chamber including a first imaging device attachable to one end of the workpiece to move with said one end and a second imaging device attachable to the other end of the workpiece to move with said other end;
   (c) means for selectively changing and monitoring the temperature of the workpiece;
   (d) a dual channel laser interferometer system including a source of first and second measurement laser beams of different frequencies placed in operative association with the workpiece so that, under testing conditions, the first beam is reflected off said first imaging device and the second beam is reflected off said second imaging device, said imaging devices moving with said ends to induce frequency shifts in said beams from which information concerning the length of the workpiece is obtained; and
   (e) a data acquisition system for computing the coefficient of thermal expansion of the workpiece based on the temperature and length of the workpiece under test.

2. An assembly according to claim 1, wherein the chamber comprises inner and outer walls which form a water jacket for heating and cooling the workpiece.

3. An assembly according to claim 1, wherein the means for changing the temperature of the workpiece comprises:
   (a) a constant temperature bath and circulator; and
   (b) pump means for evacuating the chamber.

4. An assembly according to claim 3, wherein the constant temperature bath is controlled to within ±0.5° F.

5. An assembly according to claim 4, wherein the constant temperature bath is controlled to within ±0.041° F.

6. An assembly according to claim 3, wherein the chamber is evacuated to below $1 \times 10^{-1}$ Torr.

7. An assembly according to claim 6, wherein the chamber is evacuated to below $1 \times 10^{-2}$ Torr.

8. An assembly according to claim 1, comprising at least one temperature sensing device.

9. An assembly according to claim 8, wherein the means for monitoring the temperature of the workpiece comprises at least one thermistor attachable to the workpiece.

10. An assembly as in claim 1, wherein said first imaging device comprises a device having a center, first and third quadrants positioned diagonally oppositely about said center, and first and second specular reflector portions respectively located in said first and third quadrants and having corresponding parts separated by a 180° angle; and said dual channel laser interferometer system is placed in operative association with the workpiece so that the first beam is serially reflected first from said first portion, then from said second portion.

11. An assembly as in claim 10, wherein said first imaging device further comprises second and fourth quadrants positioned diagonally oppositely about said center and first and second non-reflective portions respectively located in said second and fourth quadrants and having corresponding parts separated by a 180° angle; and said dual channel laser interferometer system is placed in operative association with the workpiece so that the second beam is serially reflected by said second imaging device first through said first non-reflective portion of said first imaging device, then through said second non-reflective portion.

12. An assembly as in claim 10, wherein said means for locating the workpiece further comprises first and second flexure systems which engage respective ends of said workpiece by way of said first and second imaging devices.

13. An assembly suitable for determining a coefficient of thermal expansion of a workpiece, the assembly comprising:
   (a) a chamber which surrounds and is spaced apart from the workpiece;
   (b) means for locating the workpiece comprising a rail assembly; a first and second flexure system connected to the rail assembly; and means for engaging the workpiece to the first and second flexure system;
   (c) means for selectively changing and monitoring the temperature of the workpiece;
   (d) a dual channel laser interferometer system placed in operative association with the workpiece so that, under testing conditions, information concerning the length of the workpiece is obtained; and
   (e) a data acquisition system for computing the coefficient of thermal expansion of the workpiece based on the temperature and length of the workpiece under test.

14. An assembly suitable for determining a coefficient of thermal expansion of a workpiece, the assembly comprising:
   (a) a chamber which surrounds and is spaced apart from the workpiece;
   (b) means for locating the workpiece in the chamber;
   (c) means for selectively changing and monitoring the temperature of the workpiece;
   (d) a dual channel laser interferometer system placed in operative association with the workpiece so that, under testing conditions, information concerning the length of the workpiece is obtained; and
   (e) a data acquisition system for computing the coefficient of thermal expansion of the workpiece based on the temperature and length of the workpiece under test;

wherein the dual channel laser interferometer system comprises:
   a two-frequency laser beam;
   a dilatometer converter for splitting the laser beam into a first frequency measurement beam and a second frequency measurement beam;
   a remote interferometer comprising a first and second reflector for optically processing the first and second frequency measurement beams respectively;
   a plane mirror converter for optically processing the beams outputted by the remote interferometer; and
   (i) a first imaging device comprising a first and second specular reflector for reflecting the first frequency measurement beam to the interferometer first and second reflectors, the first imaging device attachable to the workpiece at a first location, and capable of moving with the workpiece as the workpiece expands or contracts in response to a changing temperature; and
   (ii) a second imaging device comprising a specular reflector for reflecting the second frequency measurement beam to the first and second interferometer reflectors, the second imaging device attachable to the workpiece at a second location, and capable of moving with the workpiece as the workpiece expands or contracts in response to a changing temperature.

15. An assembly according to claim 14, wherein the duel channel laser interferometer system further comprises means:
   (i) for detecting frequency shifts in the first and second frequency measurement beams respectively induced by movements of the workpiece;
   (ii) for converting the respective frequency shifts into displacement parameters; and
   (iii) for computing the relative displacement between the first and second imaging devices based on the displacement parameters.

16. A method for determining a coefficient of thermal expansion of a workpiece having opposite ends, which method comprises:
   (a) locating the workpiece in a chamber which surrounds and is spaced apart from the workpiece, including attaching a first imaging device to one end of the workpiece to move with said one end and a second imaging device to the other end of the workpiece to move with said other end;
   (b) changing the temperature of the chamber, which in turn, causes the temperature of the workpiece to change from an arbitrary and known state to a measurable isothermal state; and (c) placing in operative association with the workpiece a dual channel laser interferometer system having first and second measurement laser beams of different frequencies, with the first beam being reflected off said first imaging device and the second beam being reflected off said second imaging device, said imaging devices moving with said ends to induce frequency shifts in said beams for obtaining information concerning the change in length of the workpiece, as the chamber temperature changes from the arbitrary and know state to the isothermal state.

17. A method according to claim 16, wherein the workpiece comprises a composite.

18. A method according to claim 17, wherein the composite comprises graphite/epoxy.

19. A method for determining a coefficient of thermal expansion of a workpiece, said method comprising:
(a) locating the workpiece in a chamber which surrounds and is spaced apart from the workpiece;
(b) changing the temperature of the chamber, which in turn, causes the temperature of the workpiece to change from an arbitrary and known state to a measurable isothermal state; and
(c) placing in operative association with the workpiece a dual channeled laser beam for obtaining information concerning the change in length of the workpiece, as the chamber temperature changes from the arbitrary and known state to the isothermal state; and
wherein said locating step further comprises:
(i) attaching a first imaging device to the workpiece at a first location, the first imaging device moving with the workpiece as the workpiece expands or contracts in response to a changing temperature, the first imaging device comprising first and second specular portions; and
(ii) attaching a second imaging device to the workpiece at a second location, the second imaging device moving with the workpiece as the workpiece expands or contracts in response to a changing temperature, the second imaging device comprising a specular reflector; and
wherein said placing step further comprises:
splitting the dual channel laser beam into a first frequency measurement beam and a second frequency measurement beam, for reflecting the first beam off the first imaging device and the second beam off the second imaging device, as the workpiece expands or contracts.

20. A method for determining a coefficient of thermal expansion of a workpiece, said method comprising:
(a) locating the workpiece in a chamber which surrounds and is spaced apart from the workpiece;
(b) changing the temperature of the chamber, which in turn, causes the temperature of the workpiece to change from an arbitrary and known state to a measurable isothermal state; and
(c) placing in operative association with the workpiece a dual channeled laser beam for obtaining information concerning the change in length of the workpiece, as the chamber temperature changes from the arbitrary and known state to the isothermal state;
wherein the step of locating the workpiece in the chamber comprises providing a rail and flexure system for positioning the workpiece and the laser beam in a known configuration, independent of changes in the length of the workpiece as it responds to the changing temperature of the chamber.

* * * * *

UNITED STATES PATENT AND TRADEMARK OFFICE
CERTIFICATE OF CORRECTION

PATENT NO. : 4,924,477
DATED : May 8, 1990
INVENTOR(S) : James F. Gilmore et al.

It is certified that error appears in the above-identified patent and that said Letters Patent is hereby corrected as shown below:

| | |
|---|---|
| Col. 3, line 9 | delete "lenght" and substitute therefor --length--; |
| Col. 3, line 18 | delete "Wolf" and substitute therefor --Wolff--; |
| Col. 3, line 21 | delete "Wolfe" and substitute therefor --Wolff--; |
| Col. 9, line 11 | delete "know" and substitute therefor --known--. |

Signed and Sealed this

Eighteenth Day of June, 1991

*Attest:*

HARRY F. MANBECK, JR.

*Attesting Officer*     *Commissioner of Patents and Trademarks*